US010531835B2

(12) United States Patent
Al-Ali et al.

(10) Patent No.: US 10,531,835 B2
(45) Date of Patent: *Jan. 14, 2020

(54) PULSE OXIMETER ACCESS APPARATUS AND METHOD

(71) Applicant: MASIMO CORPORATION, Irvine, CA (US)

(72) Inventors: Ammar Al-Ali, San Juan Capistrano, CA (US); Ronald Coverston, Portola Hills, CA (US); Massi E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 15/686,756

(22) Filed: Aug. 25, 2017

(65) Prior Publication Data

US 2018/0028124 A1 Feb. 1, 2018

Related U.S. Application Data

(63) Continuation of application No. 14/790,454, filed on Jul. 2, 2015, now Pat. No. 9,743,887, which is a continuation of application No. 12/360,830, filed on Jan. 27, 2009, now Pat. No. 9,072,474, which is a continuation of application No. 10/981,186, filed on Nov. 4, 2004, now Pat. No. 7,483,729.

(60) Provisional application No. 60/517,954, filed on Nov. 5, 2003.

(51) Int. Cl.
*A61B 5/1455* (2006.01)
*A61B 5/00* (2006.01)

(52) U.S. Cl.
CPC ........ *A61B 5/7221* (2013.01); *A61B 5/14551* (2013.01); *A61B 5/7271* (2013.01); *A61B 2560/0266* (2013.01); *A61B 2560/0475* (2013.01); *A61B 2562/08* (2013.01); *A61B 2562/221* (2013.01); *A61B 2562/222* (2013.01)

(58) Field of Classification Search
CPC .............. A61B 5/1455; A61B 5/14551; A61B 5/14552
See application file for complete search history.

(56) References Cited

U.S. PATENT DOCUMENTS

| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |

(Continued)

*Primary Examiner* — Eric F Winakur
(74) *Attorney, Agent, or Firm* — Knobbe, Martens, Olson & Bear LLP

(57) ABSTRACT

Access is provided to certain pulse oximetry systems utilizing a keyed sensor and a corresponding locked sensor port of a restricted access monitor. In such systems, the keyed sensor has a key comprising a memory element, and the monitor has a memory reader associated with the sensor port. The monitor is configured to function only when the key is in communications with the locked sensor port, and the memory reader is able to retrieve predetermined data from the memory element. The monitor is accessed by providing the key separate from the keyed sensor, integrating the key into an adapter cable, and connecting the adapter cable between the sensor port and an unkeyed sensor so that the monitor functions with the unkeyed sensor.

11 Claims, 6 Drawing Sheets

(56) References Cited

U.S. PATENT DOCUMENTS

| | | |
|---|---|---|
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,685,299 A | 11/1997 | Diab et al. |
| 5,720,293 A | 2/1998 | Quinn et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,807,247 A | 9/1998 | Merchant et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,490,466 B1 | 12/2002 | Fein et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,708,049 B1 | 3/2004 | Berson et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |

(56) References Cited

U.S. PATENT DOCUMENTS

| | | |
|---|---|---|
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |

PULSE OXIMETER ACCESS APPARATUS AND METHOD

REFERENCE TO RELATED APPLICATIONS

The present application claims priority benefit under 35 U.S.C. § 120 to, and is a continuation of U.S. patent application Ser. No. 14/790,454, filed Jul. 2, 2015 entitled "Pulse Oximeter Access Apparatus and Method," which claims priority benefit under 35 U.S.C. § 120 to, and is a continuation of U.S. patent application Ser. No. 12/360,830, filed Jan. 27, 2009 entitled "Pulse Oximeter Access Apparatus and Method," which claims priority benefit under 35 U.S.C. § 120 to, and is a continuation of U.S. patent application Ser. No. 10/981,186, filed Nov. 4, 2004 entitled "Pulse Oximeter Access Apparatus and Method," now U.S. Pat. No. 7,482,729, which claims priority benefit under 35 U.S.C. § 119(e) from U.S. Provisional Application No. 60/517,954, filed Nov. 5, 2003, entitled "Pulse Oximeter Access Apparatus and Method." The present application also incorporates the foregoing disclosures herein by reference.

BACKGROUND OF THE INVENTION

Pulse oximeters have gained rapid acceptance in a wide variety of medical applications, including surgical wards, intensive care units, general wards and home care by providing early detection of decreases in the arterial oxygen supply, reducing the risk of accidental death and injury. FIG. 1 illustrates a pulse oximetry system 100 having a sensor 110 applied to a patient 10, a monitor 160, and a patient cable 140 connecting the sensor 110 and the monitor 160. The sensor 110 has a sensor body 111 that houses emitters and a detector and is attached to a patient at a selected fleshy medium site, such as a fingertip or ear lobe. The emitters are positioned to project light of at least two wavelengths through the blood vessels and capillaries of the fleshy medium. The detector is positioned so as to detect the emitted light after absorption by the fleshy medium, including hemoglobin and other constituents of pulsatile blood flowing within the fleshy medium, and generate at least first and second intensity signals in response. The sensor 110 has a patient cable connector 114 and may have an integrated sensor cable 112. The sensor 110 may be a disposable adhesive sensor for use on a single patient or a reusable clip-on sensor for use on multiple patients.

As shown in FIG. 1, the monitor 160, which may be a standalone device or may be incorporated as a module or built-in portion of a multiparameter patient monitoring system, computes at least one physiological parameter responsive to magnitudes of the intensity signals. A monitor 160 typically provides a numerical readout of the patient's oxygen saturation 164, a numerical readout of pulse rate 166, and a display the patient's plethysmograph 168, which provides a visual display of the patient's pulse contour and pulse rate. The monitor 160 has a sensor port 162 that transmits emitter drive signals to the sensor 110 and receives the detector intensity signals from the sensor 110. The patient cable 140 provides the electrical and mechanical connection and communications link between the sensor port 162 and the sensor 110. The patient cable 140 has a sensor connector 142 that connects to the patient cable connector 114 and a monitor connector 144 that connects to the sensor port 162.

Pulse oximeters have gained rapid acceptance in a wide variety of medical applications, including surgical wards, intensive care units, general wards and home care by providing early detection of decreases in the arterial oxygen supply, reducing the risk of accidental death and injury. FIG. 1 illustrates a pulse oximetry system 100 having a sensor 110 applied to a patient 10, a monitor 160, and a patient cable 140 connecting the sensor 110 and the monitor 160. The sensor 110 has a sensor body 111 that houses emitters and a detector and is attached to a patient at a selected fleshy medium site, such as a fingertip or ear lobe. The emitters are positioned to project light of at least two wavelengths through the blood vessels and capillaries of the fleshy medium. The detector is positioned so as to detect the emitted light after absorption by the fleshy medium, including hemoglobin and other constituents of pulsatile blood flowing within the fleshy medium, and generate at least first and second intensity signals in response. The sensor 110 has a patient cable connector 114 and may have an integrated sensor cable 112. The sensor 110 may be a disposable adhesive sensor for use on a single patient or a reusable clip-on sensor for use on multiple patients.

As shown in FIG. 1, the monitor 160, which may be a standalone device or may be incorporated as a module or built-in portion of a multiparameter patient monitoring system, computes at least one physiological parameter responsive to magnitudes of the intensity signals. A monitor 160 typically provides a numerical readout of the patient's oxygen saturation 164, a numerical readout of pulse rate 166, and a display the patient's plethysmograph 168, which provides a visual display of the patient's pulse contour and pulse rate. The monitor 160 has a sensor port 162 that transmits emitter drive signals to the sensor 110 and receives the detector intensity signals from the sensor 110. The patient cable 140 provides the electrical and mechanical connection and communications link between the sensor port 162 and the sensor 110. The patient cable 140 has a sensor connector 142 that connects to the patient cable connector 114 and a monitor connector 144 that connects to the sensor port 162.

SUMMARY OF THE INVENTION

FIG. 2 illustrates a restricted access pulse oximetry system 200 having a keyed sensor 210 and a restricted access monitor 260. The keyed sensor 210 and restricted access monitor 260 are designed so that the monitor 260 will only function with a specific sensor or family of sensors from a specific manufacturer or licensed vendors. Upon power up, the sensor port 262 is locked. That is, the monitor 260 will not function until it reads the correct information from the sensor port 262. In particular, a patient cable connector 214 has a memory device. The memory device and the data stored in the memory device act as a key. The sensor port 262 and a memory reader in the monitor associated with the sensor port 262 act as a lock. When the keyed patient cable connector 214 is in communications with the locked sensor port 262 via a patient cable 240, the memory reader can access the data stored in the memory device. If the stored data matches predetermined access data, the monitor unlocks the sensor port 262, i.e. properly functions with a sensor attached to the sensor port 262. A memory device commonly used for storing manufacturer and product information is the DS2502 from Dallas Semiconductor, which has a 1 kbit memory that is accessed through a single pin that provides data input, data output and power. Once the sensor port 262 is unlocked, the sensor 210, patient cable 240, sensor port 262 and monitor 260 function as described with respect to FIG. 1, above.

One aspect of a pulse oximeter access method is used in conjunction with a pulse oximetry system comprising a keyed sensor and a corresponding locked sensor port of a restricted access monitor. The keyed sensor has a key comprising a memory element. The monitor has a memory reader associated with the sensor port. The monitor is configured to function only when the key is in communications with the locked sensor port and the memory reader is able to retrieve predetermined data from the memory element. The access method comprises the steps of providing the key separate from the keyed sensor, integrating the key into an adapter cable, and connecting the adapter cable between the sensor port and an unkeyed sensor so that the monitor functions with the unkeyed sensor.

Another aspect of a pulse oximeter access apparatus comprises a sensor having emitters adapted to transmit light of at least first and second wavelengths into a fleshy medium and a light sensitive detector adapted to generate at least first and second intensity signals by detecting the light after absorption by constituents of pulsatile blood flowing within the fleshy medium. A monitor is configured to non-invasively measure one or more physiological parameters responsive to magnitudes of the intensity signals. A key contains access information. A sensor port is configured to communicate emitter drive signals from the monitor to the sensor, intensity signals from the sensor to the monitor, and the access information from the key to the monitor. A lock associated with the sensor port is adapted to read the access information from the key and to enable the monitor to provide measurements of the physiological parameters in response to the access information. An adapter cable containing the key is configured to provide a communications link between the sensor and the sensor port.

A further aspect of a pulse oximeter access apparatus comprises a sensor means for providing a physiological signal to a monitor and a key means for providing access to a locked sensor port portion of the monitor. An adapter cable means containing the key means provides communications between the sensor and the sensor port.

DETAILED DESCRIPTION OF THE PREFERRED EMBODIMENT

Figure 3:
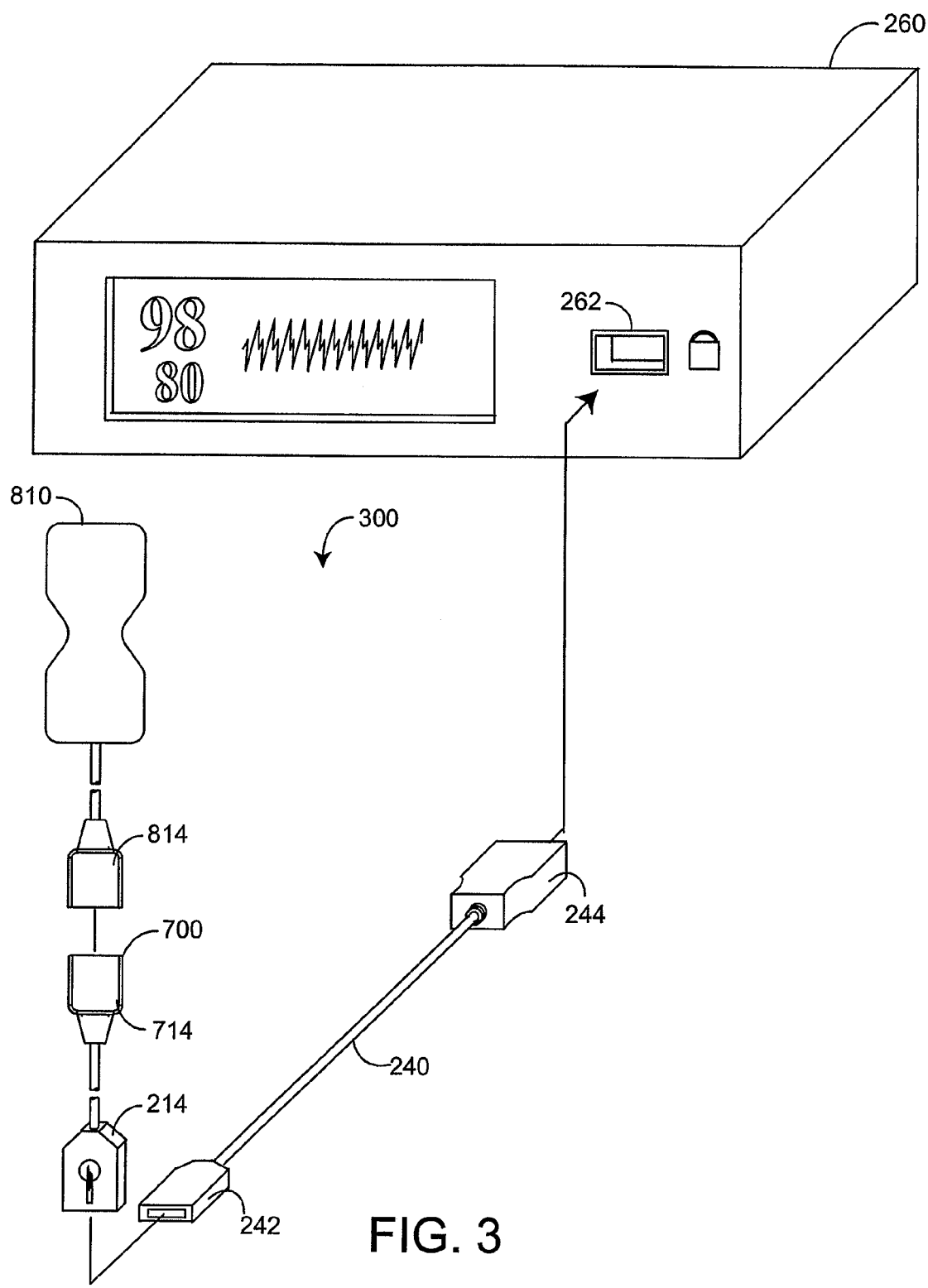
FIG. 3 is a perspective view of a pulse oximeter access apparatus.

FIG. 3 illustrates a pulse oximeter access apparatus 300 having a keyless sensor 810, a keyed adapter cable 700 and a patient cable 240 that advantageously interconnect so as to allow the keyless sensor 810 to function with a restricted access monitor 260 having a locked sensor port 262. The keyed adapter cable 700 has a keyed connector 214 at one end, which mates with a sensor connector 242 of a patient cable 240, and a sensor connector 714 at the opposite end, which mates with a patient cable connector 814 of the keyless sensor 810. The monitor connector 244 mates with the sensor port 262, providing communications between the keyless sensor 810 and the sensor port 262 and between a memory element in the keyed connector 214 and a memory reader within the monitor 260. The sensor connector 714 of the keyed adapter cable 700 can be any of a number of connectors that mate with any of a number of patient cable connectors 814. Further, a family of keyed adapter cables 700 can be configured, each with a different sensor connector 714 compatible with a different keyless sensor 810 or family of keyless sensors 810.

Figure 4:
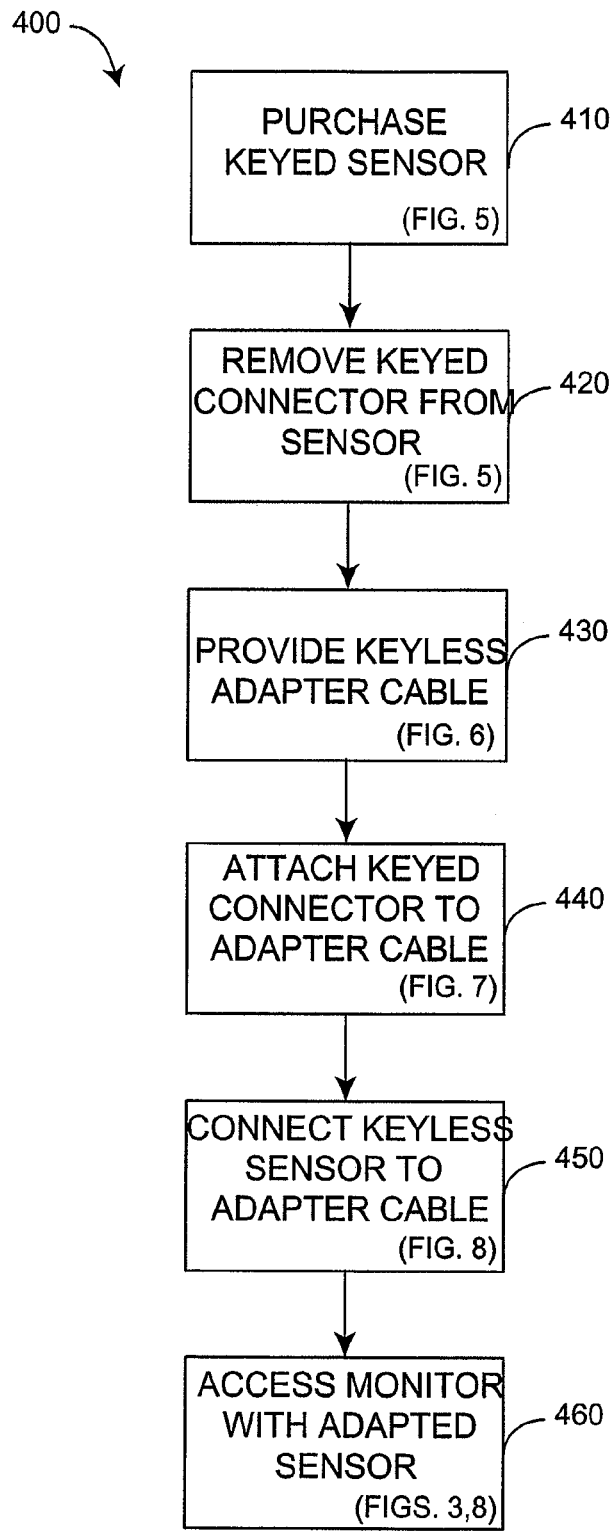
FIG. 4 is a flow diagram of a pulse oximeter access method.
Figure 6:
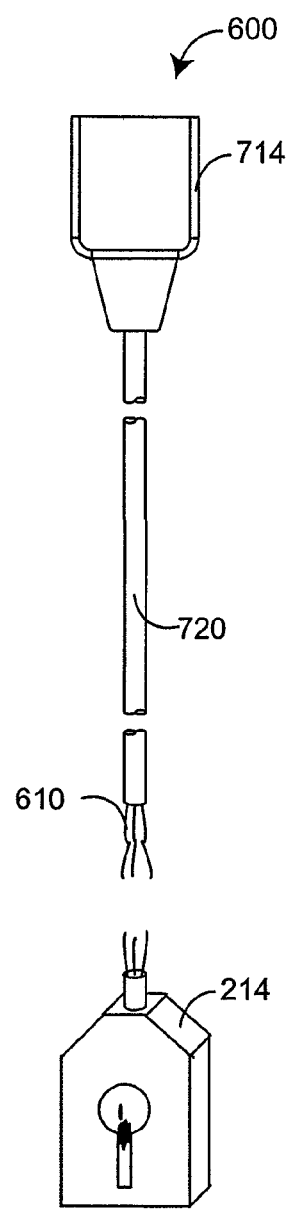
Figure 7:
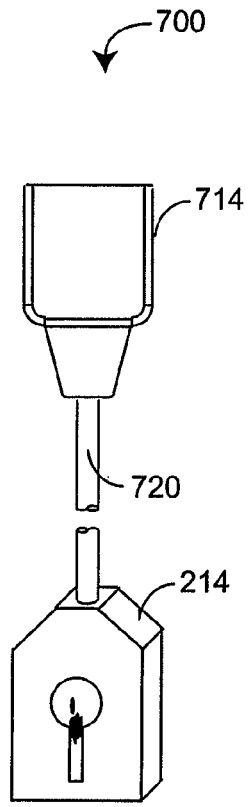
FIGS. 7-8 are perspective views of a keyed adapter cable and an attached keyless sensor, respectively.

FIG. 4 illustrates a pulse oximeter access method 400 for creating and utilizing a keyed adapter cable 700 (FIGS. 3, 7). In an initial step, a sensor port key is provided by purchasing 410 a keyed sensor configured for a particular restricted access monitor 260 (FIG. 2) and removing 420 the associated keyed connector 214 (FIG. 2), as described in further detail with respect to FIG. 5, below. Further steps include providing 430 a keyless adapter cable 600 (FIG. 6), and attaching 440 the keyed connector 214 (FIG. 2) to one end to make the keyed adapter cable 700 (FIG. 7), as described in further detail with respect to FIGS. 6-7, below. Additional steps include connecting 450 a keyless sensor 810 (FIG. 8) to the keyed adapter cable, and accessing 460 the restricted access monitor with the resulting adapted sensor 800 (FIG. 8), as described in further detail with respect to FIG. 3, above, and FIG. 8, below.

Figure 5:
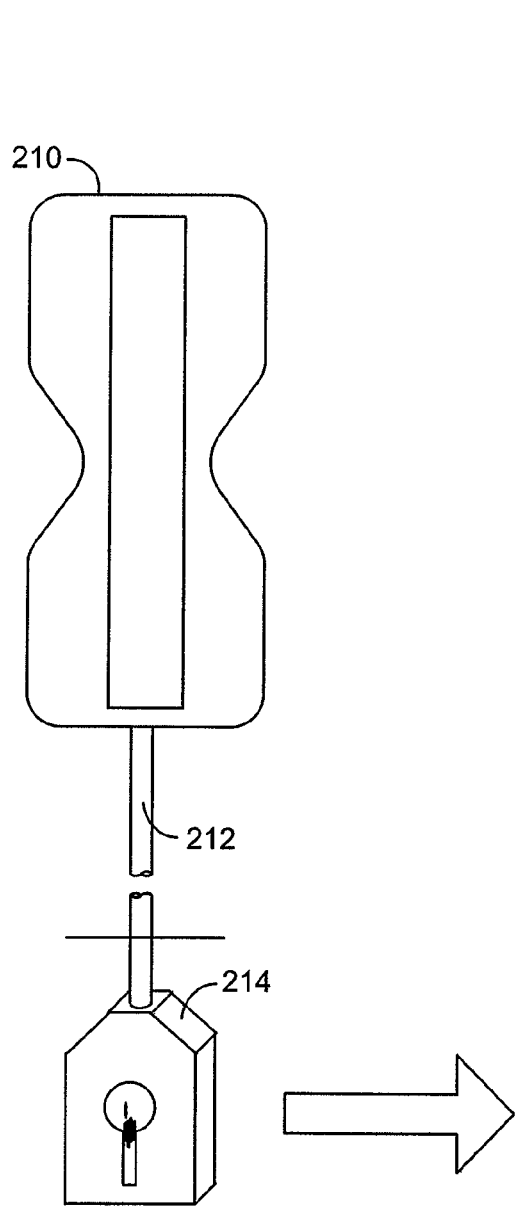
FIGS. 5-6 are perspective views of a keyed sensor and a keyless adapter cable, respectively, illustrating lock removal and reattachment.

FIGS. 5-6 illustrate obtaining a sensor key from a keyed sensor 210 (FIG. 5) and using the key in the construction of a keyed adapter cable 700 (FIG. 7). As shown in FIG. 5, the keyed connector 214 is removed from a keyed sensor 210, such as by cutting the sensor cable 212 so as to leave sufficient wire for reattachment. As shown in FIG. 6, a keyless adapter cable 600 is provided having a cable 720 with a sensor connector 714 attached to a first end and with unconnected wires 610 at a second end. The removed keyed connector 214 is spliced or otherwise attached to the second end by any of various well-known methods, such as soldering or crimping followed by heat-shrink insulation to name a few techniques.

Construction of a keyed adapter cable 700 (FIG. 7) is described above with respect to removal and reattachment of a keyed connector 214. In an alternative embodiment, the key or memory element itself is removed from the keyed connector 214 of a keyed sensor 210 (FIG. 5) and embedded into or otherwise integrated into or incorporated with either one or both connectors of an otherwise keyless adapter cable 600 to construct the keyed adapter cable 700 (FIG. 7). In yet another embodiment, an equivalent memory element is purchased, developed or otherwise obtained and programmed with access data compatible with the memory element of the keyed sensor 210 (FIG. 5) and embedded into or otherwise integrated into or incorporated with either one or both connectors of an otherwise keyless adapter cable 600 to construct the keyed adapter cable 700 (FIG. 7).

FIG. 7 illustrates a keyed adapter cable 700 having a sensor connector 714, a keyed connector 214 and a cable 720 interconnecting the sensor connector 714 and keyed connector 214. The sensor connector 714 is configured to connect to a sensor patient cable connector 814 (FIG. 8), and the keyed connector 214 is configured to connect to a patient cable sensor connector 242 (FIG. 3). The keyed connector 214 has a memory element that is readable by a restricted access monitor 260 (FIG. 3) so as to unlock a locked sensor port 262 (FIG. 3), as described above.

Figure 1:
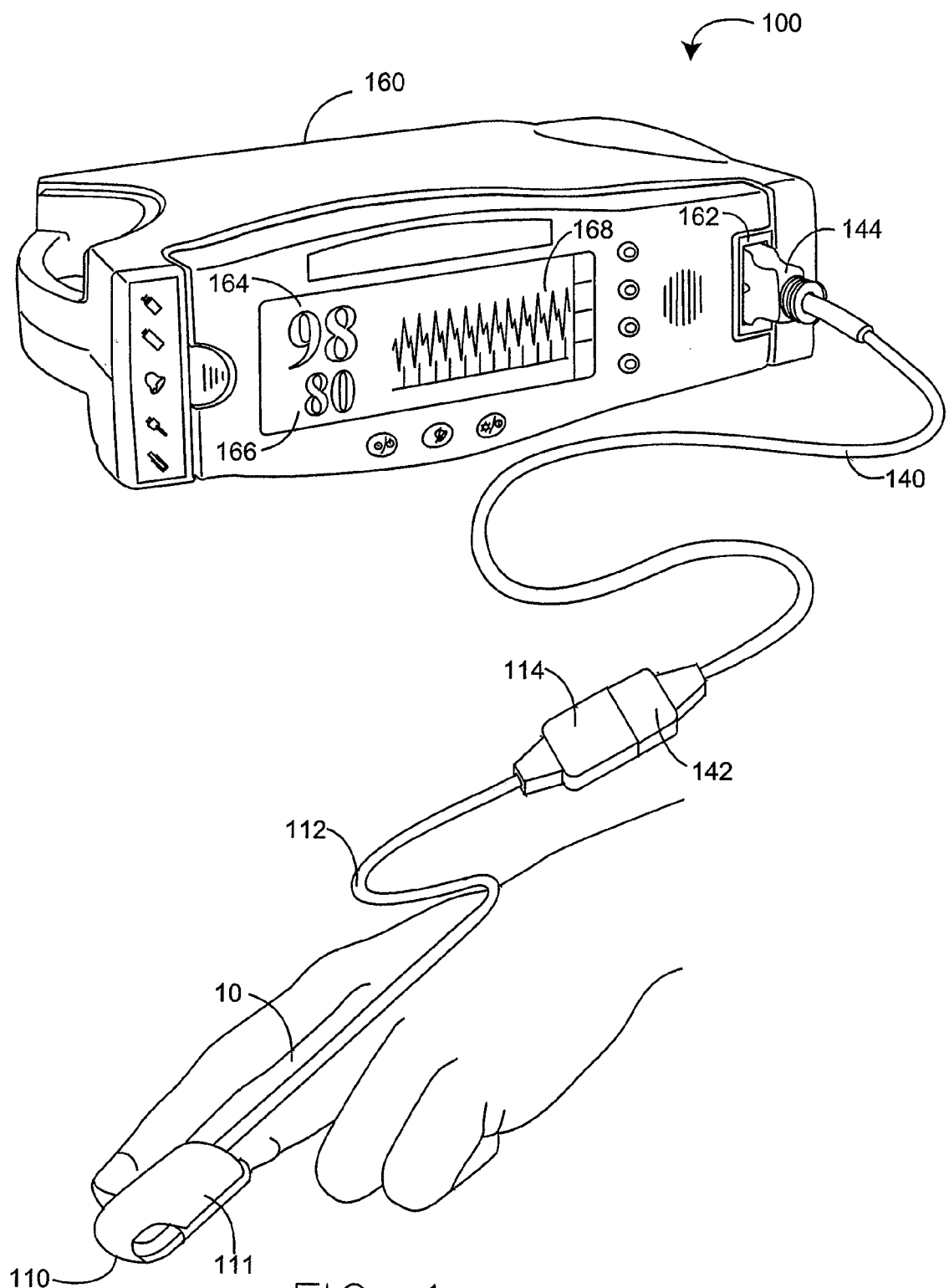
FIG. 1 is a perspective view of a prior art pulse oximetry system.
Figure 2:
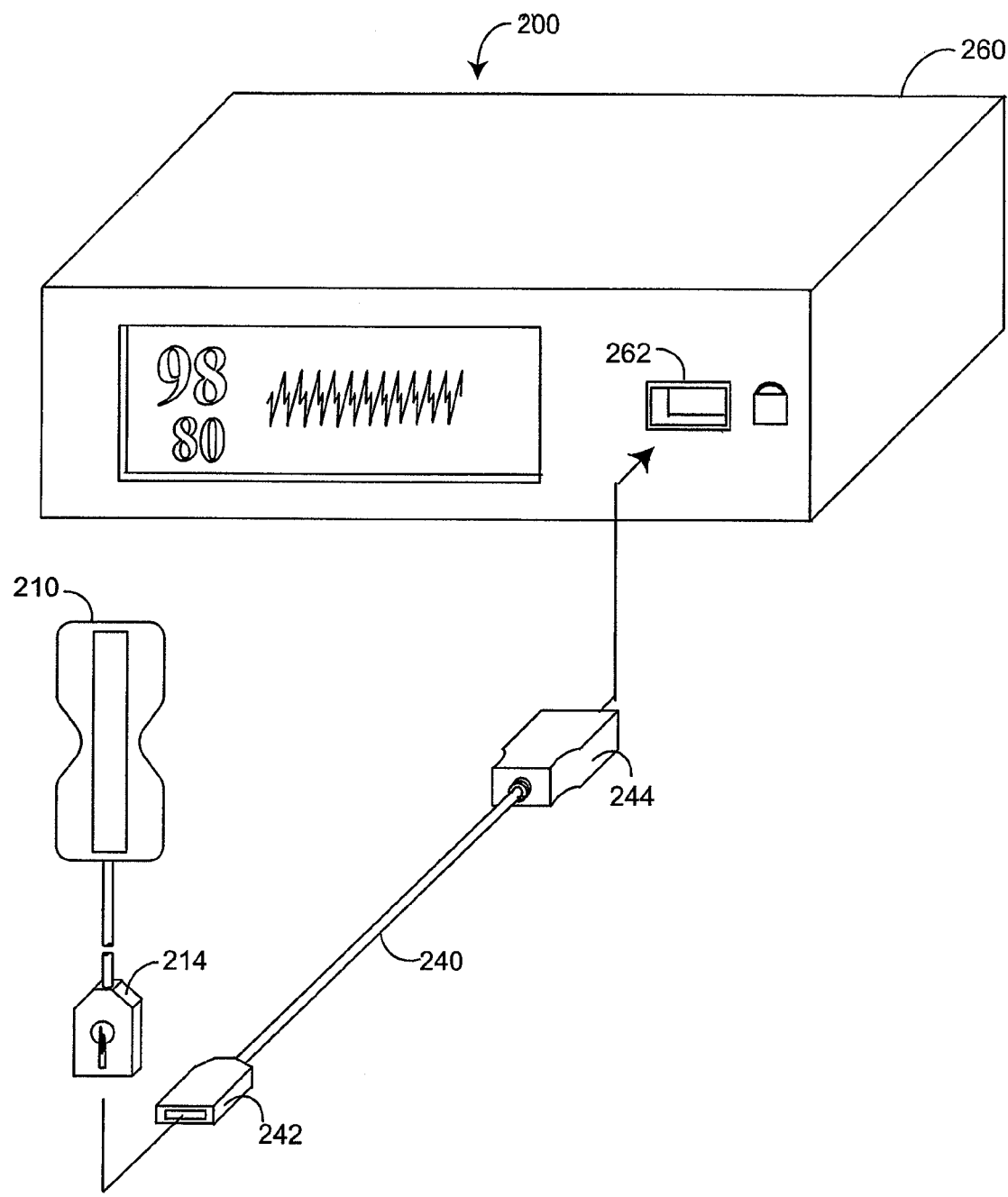
FIG. 2 is a perspective view of a prior art pulse oximetry system having a restricted access monitor with a locked sensor port.
Figure 8:
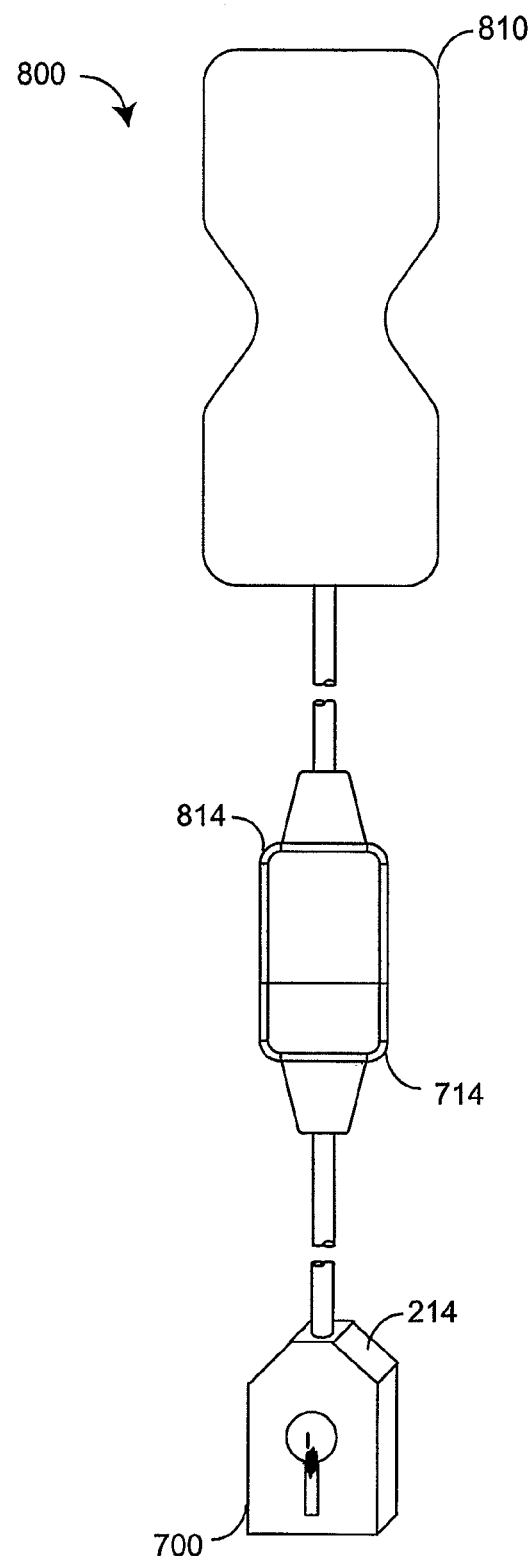

FIG. 8 illustrates an adapted sensor 800 having a keyed adapter cable 700 attached to a keyless sensor 810. The sensor connector 714 of the keyed adapter cable 700 is mated to the patient cable connector 814 of the keyless sensor 810. The resulting adapted sensor 800 is configured to function with a restricted access monitor 260 (FIG. 3) in an equivalent manner as a keyed sensor 210 (FIG. 2). In particular, the keyed connector 214 mates with a patient cable 240 (FIG. 3), which mates with a locked sensor port 262 (FIG. 3) of a restricted access monitor 260 (FIG. 3) so that monitor 260 (FIG. 3) functions with the keyless sensor 810, as described above with respect to FIG. 3.

A keyed adapter cable is described above with respect to an adapter between a keyless sensor 810 and a patient cable 240 (FIG. 3). Such an embodiment is particularly advantageous for utilization of a keyed connector 214 removed from a keyed sensor 210 (FIG. 5). In an alternative embodiment, the patient cable 240 (FIG. 3) itself is utilized as a keyed adapter cable between a keyless sensor 810 and a locked sensor port 262 (FIG. 3). In particular, a memory element containing access data is removed from a keyed sensor 210 (FIG. 5) or a memory element is purchased, developed or otherwise obtained and programmed with compatible access data. The memory element is embedded into or otherwise integrated into or incorporated with either one or both connectors of an otherwise keyless patient cable 240 (FIG. 3) to construct a keyed adapter cable.

A pulse oximeter access apparatus and method has been disclosed in detail in connection with various embodiments. These embodiments are disclosed by way of examples only and are not to limit the scope of the claims that follow. One of ordinary skill in art will appreciate many variations and modifications.

What is claimed is:

1. A method of utilizing a memory device, the memory device storing access information usable to unlock otherwise unavailable processing by a patient monitor so that the patient monitor processes a signal output by a noninvasive optical sensor to determine a physiological parameter of a patient monitored by the noninvasive optical sensor, the method comprising:

acquiring a first sensor apparatus comprising a first noninvasive optical sensor and a memory device, the first noninvasive optical sensor comprising a first detector configured to output a first signal responsive to attenuation of light by tissue of a patient, the memory device storing access information usable to unlock otherwise unavailable processing of the first signal by a patient monitor, the patient monitor being configured to lock processing of the first signal by the patient monitor unless the access information is received by the patient monitor;

removing the memory device from the first sensor apparatus so that electrical communication between the memory device and the first sensor apparatus is severed; and subsequent to said removing the memory device from the first sensor apparatus, attaching the memory device to an assembly configured to support the memory device and couple to a second sensor apparatus comprising a second noninvasive optical sensor, the second noninvasive optical sensor comprising a second detector configured to output a second signal responsive to attenuation of light by the tissue, the second sensor apparatus together with the assembly being configured to communicate the access information to the patient monitor without the first noninvasive optical sensor and being usable to unlock otherwise unavailable processing of the second signal by the patient monitor, the patient monitor being configured to lock processing of the second signal by the patient monitor unless the access information is received by the patient monitor.

2. The method of claim 1, wherein said attaching the memory device to the assembly comprises soldering the memory device to the assembly.

3. The method of claim 1, wherein said attaching the memory device to the assembly comprises crimping the memory device to the assembly.

4. The method of claim 1, wherein said attaching the memory device to the assembly comprises embedding the memory device inside the assembly.

5. The method of claim 1, wherein the assembly comprises a cable.

6. The method of claim 1, wherein the assembly comprises a connector.

7. The method of claim 1, further comprising coupling a connector interface of the second sensor apparatus to a corresponding interface of the assembly.

8. The method of claim 1, further comprising connecting the patient monitor to the assembly so that the second sensor apparatus together with the memory device communicates the access information to the patient monitor to unlock processing of the second signal by the patient monitor.

9. The method of claim 8, further comprising communicating the second signal from the second sensor apparatus to the patient monitor through the assembly.

10. The method of claim 1, further comprising:

receiving, with the patient monitor, the access information from the memory device; and in response to receiving the access information from the memory device, determining, with the patient monitor, to process the second signal from the second noninvasive optical sensor and subsequently processing the second signal to determine a physiological parameter of the patient.

11. The method of claim 1, wherein the access information is predetermined.

* * * * *

UNITED STATES PATENT AND TRADEMARK OFFICE
CERTIFICATE OF CORRECTION

PATENT NO. : 10,531,835 B2
APPLICATION NO. : 15/686756
DATED : January 14, 2020
INVENTOR(S) : Al-Ali et al.

Page 1 of 1

It is certified that error appears in the above-identified patent and that said Letters Patent is hereby corrected as shown below:

In the Specification

In Column 1, Line 17, delete "7,482,729" and insert --7,483,729--.

Signed and Sealed this
Fourteenth Day of April, 2020

Andrei Iancu
*Director of the United States Patent and Trademark Office*